(12) United States Patent
Veldman (10) Patent No.: US 6,517,505 B1
(45) Date of Patent: Feb. 11, 2003

(54) PLIABLE ORTHOTIC DEVICE

(76) Inventor: Bernie T. Veldman, 1370 Roelke Dr., South Bend, IN (US) 46614

( * ) Notice: Subject to any disclaimer, the term of this patent is extended or adjusted under 35 U.S.C. 154(b) by 0 days.

(21) Appl. No.: 09/427,531

(22) Filed: Oct. 26, 1999

(51) Int. Cl.$^7$ .................................................. A61F 5/00
(52) U.S. Cl. ................................ 602/27; 602/5; 602/6; 602/23; 602/28
(58) Field of Search ........................... 602/5–6, 10, 23, 602/27, 29, 1, 28, 41, 60, 65; 128/845, 846, 882

(56) References Cited

U.S. PATENT DOCUMENTS

| | | | |
|---|---|---|---|
| 4,446,856 A | | 5/1984 | Jordan |
| 4,672,955 A | | 6/1987 | Cooper |
| 4,776,326 A | | 10/1988 | Young et al. |
| 4,844,058 A | | 7/1989 | Vogelbach |
| 4,888,225 A | | 12/1989 | Sandvig et al. |
| 5,174,052 A | | 12/1992 | Schoenhaus et al. |
| 5,231,723 A | | 8/1993 | White et al. |
| 5,323,549 A | | 6/1994 | Segel et al. |
| 5,370,604 A | * | 12/1994 | Bernardoni ................... 602/27 |
| 5,573,501 A | | 11/1996 | Ruscito et al. |
| 5,593,383 A | | 1/1997 | DeToro |
| 5,797,862 A | * | 8/1998 | Lamont ........................ 602/10 |
| 5,810,754 A | * | 9/1998 | Kenosh ........................ 602/27 |
| 5,887,591 A | | 3/1999 | Powell et al. |

* cited by examiner

Primary Examiner—Nicholas D. Lucchesi
Assistant Examiner—Lalita M. Hamilton
(74) Attorney, Agent, or Firm—Baker & Daniels (57) ABSTRACT

The present invention relates to an orthotic for correction of foot pronation and a method to fabricate the foot orthotic. The orthotic includes a thin formable body having pliable medial and lateral side walls and a pliable bottom, and a securing mechanism to draw the side walls about a foot so as to create a hydrostatic pressure of the soft tissue of the foot within the orthotic. The securing mechanism includes hook and loop straps attached to the pliable body and looping rings attached to the pliable body for wrapping the straps therethrough. The pliable body is vacuumed formed plastic wherein the plastic is chosen form the group consisting essentially of polypropylene, polyethylene or copolymer. The orthotic has a heel post attached to the bottom thereof to provide stability for standing or walking. The heel post is formed from a semi circular piece of material chosen from the group consisting essentially of polypropylene, polyethylene, or copolymer. The pliable body is shaped to rise above the ankles of a user and to dip down posteriorly to the top of the user's heel. The foot orthotic is also designed to wrap partially over the dorsum of the foot on both the medial and lateral sides thereof so as to define a narrow gap between the medial and lateral walls as the pliable body is wrapped about the foot. The pliable body extends medially just proximal to but not encompassing the first metatarsal head of the foot and laterally just distal to and encompassing the fifth metatarsal head of the foot. The foot orthotic that may be fabricated using a cast of the foot to receive the orthotic or by taking selective measurements of the foot to receive the orthotic and choosing a positive mold from among a number of preexisting molds in accordance with the measurements.

20 Claims, 9 Drawing Sheets

PLIABLE ORTHOTIC DEVICE

BACKGROUND OF THE INVENTION

1. Field of the Invention

This invention relates to an orthotic device for bracing a foot, and in particular, to an orthotic device having a formable body which can be wrapped tightly enough around a foot to create hydrostatic pressure of the soft tissue of the foot within the walls of the orthotic device.

2. Discussion of the Prior Art

Pronation in the pediatric population has long been recognized as a significant problem. In order to address this issue, it is necessary to distinguish the difference between flat foot and a pronated foot. Although the average person may not be able to differentiate between the two, the divergence is quite clear.

A flat foot is simply a medial longitudinal arch (the main arch on the instep of the foot) which has very little curvature or vault to it. In this case, the arch will continue to maintain the shape both in weight bearing and in non-weight bearing positions.

A pronated foot, which is often mistakenly referred to as a flat foot, may very well have a nicely curved or bow-shaped medial longitudinal arch in non-weight bearing circumstances, but when the individual with a pronated foot stands or otherwise bears weight the foot flattens out. This falling or collapsing of the medial longitudinal arch is the one of the components of the pronated foot. Pronation can best be described as combinations of the heel rolling into a valgus position wherein the lower aspect of the heel angles away from the center of the body causing the inner ankles to shift in towards each other. The valgus position is worsened as the full weight of the body is brought down upon the heel. This in turn causes the mid foot to evert or flatten across the medial longitudinal arch. The end result is an abduction or shifting away of the foot from the center or midline of the body.

Pronation of the foot can cause many problems both intrinsic and extrinsic to the foot. Intrinsically, a significant amount of stress is placed on the subtalar joint (the articulation of the calcaneus talus) when the calcaneus heel rolls into a valgus position. As the mid foot everts or flattens weight bearing of the metatarsal heads is changed, creating not only stress on the joints of the mid foot, but also an undue amount of weight to be born through the lateral (outside) aspect of the foot. Extrinsically this pronation changes the angle at which the tibia (shin bone) is positioned during weight bearing causing a great deal of stress on the knee and hip joints.

Children deal with and perceive this type of stress on the joints as a fatigue and will tend to spend more time sitting instead of standing and playing on their feet. The improper positioning of the bones of the foot and ankle also serve to create a sense of instability in younger children, resulting in poor balance and poor development of upright motor skills. Hyper pronation may be observed in very young children and in some cases may be treated with casts. Most cases though, go undetected and untreated until the patient bears weight on the foot and wear shoes. Early recognition and detection of hyper pronation and control thereof is essential to allow a child with pronation to participate fully in normal activities and to preclude stress in the knees and hip joints which may cause problems as the child develops into an adult.

Uncorrected pronation can lead to the development of problems in adults intrinsic to the foot such as heel spurs, bunions, and hammer toes, as well as symptoms extrinsic to the foot such as knee pain and low back pain.

Over the years many devices have been established and marketed to combat this problem. Various types of braces, shoes and shoe supports have been developed. Shoe modifications as well as heel modifications, such as the Thomas Heel, have been utilized for years but have been relatively ineffective. An inner sole orthotic device for treating pronation is disclosed in U.S. Pat. No 5,174,052 to Schoenhaus, et al., incorporated herein by reference, but an inner sole device alone cannot provide sufficient support for children experiencing severe pronation. In addition, many devices to treat pronation are heavy, awkward, or inhibit the walking and other activities of the wearer.

Therefore, it is an object of the invention to provide a new and improved device of treating pronation, and more particularly a device particularly suited for treating the pediatric population weighing less than 85 pounds.

It is a further object of the invention to provide a device for treating pronation that is light weight and effective.

An additional object of the invention is to provide a device for treating pronation that is formable and can create hydrostatic pressure within the soft tissue of the foot to provide proper support and development.

SUMMARY OF THE INVENTION

A feature of the invention is to provide an orthotic for correction of foot pronation and a method to fabricate the foot orthotic. The orthotic includes a thin formable body having pliable medial and lateral side walls and a pliable bottom, and a securing mechanism to draw the side walls about a foot so as to create a hydrostatic pressure of the soft tissue of the foot within the orthotic.

Another feature of the invention is to have the securing mechanism include hook and loop straps attached to the pliable body and looping rings attached to the pliable body for wrapping the straps therethrough.

Also, a feature of the invention is to have the pliable body include vacuumed formed plastic wherein the plastic is chosen form the group consisting essentially of polypropylene, polyethylene or copolymer.

It is a further feature of the invention to include a heel post attached to the bottom of the foot orthotic to provide stability for standing or walking and to have the heel post formed from a semi circular piece of material chosen from the group consisting essentially of polypropylene, polyethylene, or copolymer.

An additional feature of the invention is to have the pliable body shaped to rise above the ankles of a user and to dip down posteriorly to the top of the user's heel. The foot orthotic is also designed to wrap over the dorsum of the foot on both the medial and lateral sides thereof.

Another feature of the invention is that a narrow gap is defined by the pliable body between the medial and lateral walls thereof as said pliable body is wrapped about the foot.

It is also a feature of the invention that the pliable body extends medially just proximal to but not encompassing the first metatarsal head of the foot and laterally just distal to and encompassing the fifth metatarsal head of the foot.

Lastly, it is a feature of the invention to provide a foot orthotic that may be fabricated using a cast of the foot to receive the orthotic or by taking selective measurements of the foot to receive the orthotic and choosing a positive mold from among a number of preexisting molds in accordance with the measurements.

There has thus been outlined, rather broadly, the more important features of the invention in order that the detailed description thereof that follows may be better understood, and in order that the present contribution to the art may be better appreciated. There are, of course, additional features of the invention that will be described herinafter and which will form the subject matter of the claims appended hereto.

DETAILED DESCRIPTION OF THE PREFERRED EMBODIMENT

Referring now to the drawings, a foot orthotic generally indicated at 10 holds a pronated foot 12. Foot orthotic 10 includes a pliable body generally indicated at 14, a securing mechanism generally indicated as 16, and a heel post or portion 18.

The foot orthotic 10 includes a lateral side wall 20, a medial sidewall 22, and a bottom portion 24. Lateral side wall 20 coincides with the outer or exterior portion of foot 12 and medial side wall 22 coincides with the inner portion of foot 12. Lateral and medial side walls 20, 22 are configured to rise above the ankle of a wearer of the orthotic by about ½ to 1½". When donned by a wearer, lateral and medial side walls 20, 22 also partially wrap over the top or dorsum 30 of foot 12 leaving a narrow gap of approximately ½–1" between said side walls.

Figure 7:
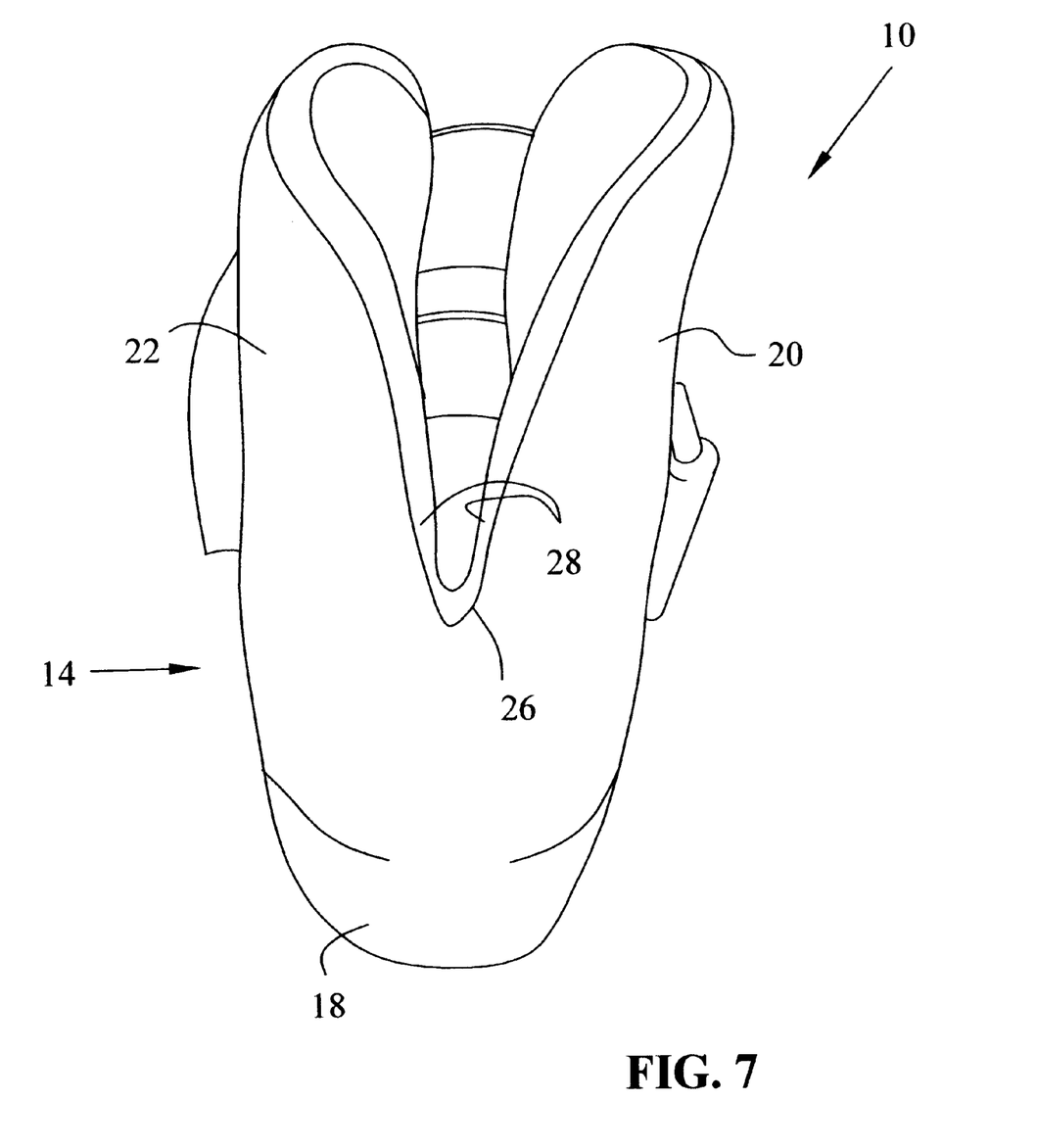
FIG. 7 is a rear view of the foot orthotic.

As best shown in FIG. 7, at the rear of foot orthotic 10, pliable body 14 dips down to a posterior point 26 which corresponds approximately to the top of the heel of the wearer of the orthotic. This results in a narrow posterior opening or gap 28 of approximately ¼–⅜" running vertically along the posterior aspect of foot orthotic 10 between the top of the heel at posterior point 26 and the top of pliable body 14.

Figure 5:
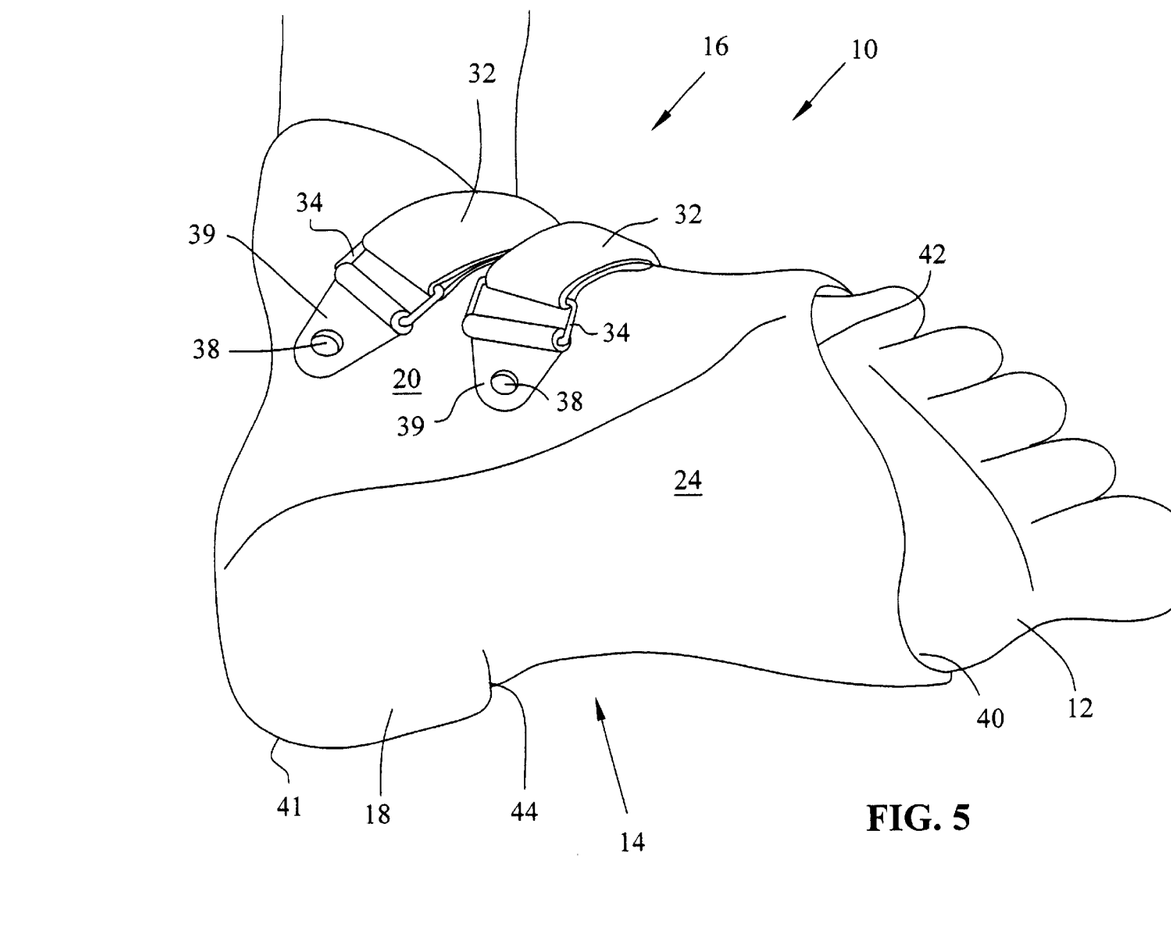
FIG. 5 is a perspective view of a foot in the foot orthotic as viewed from the bottom.
Figure 6:
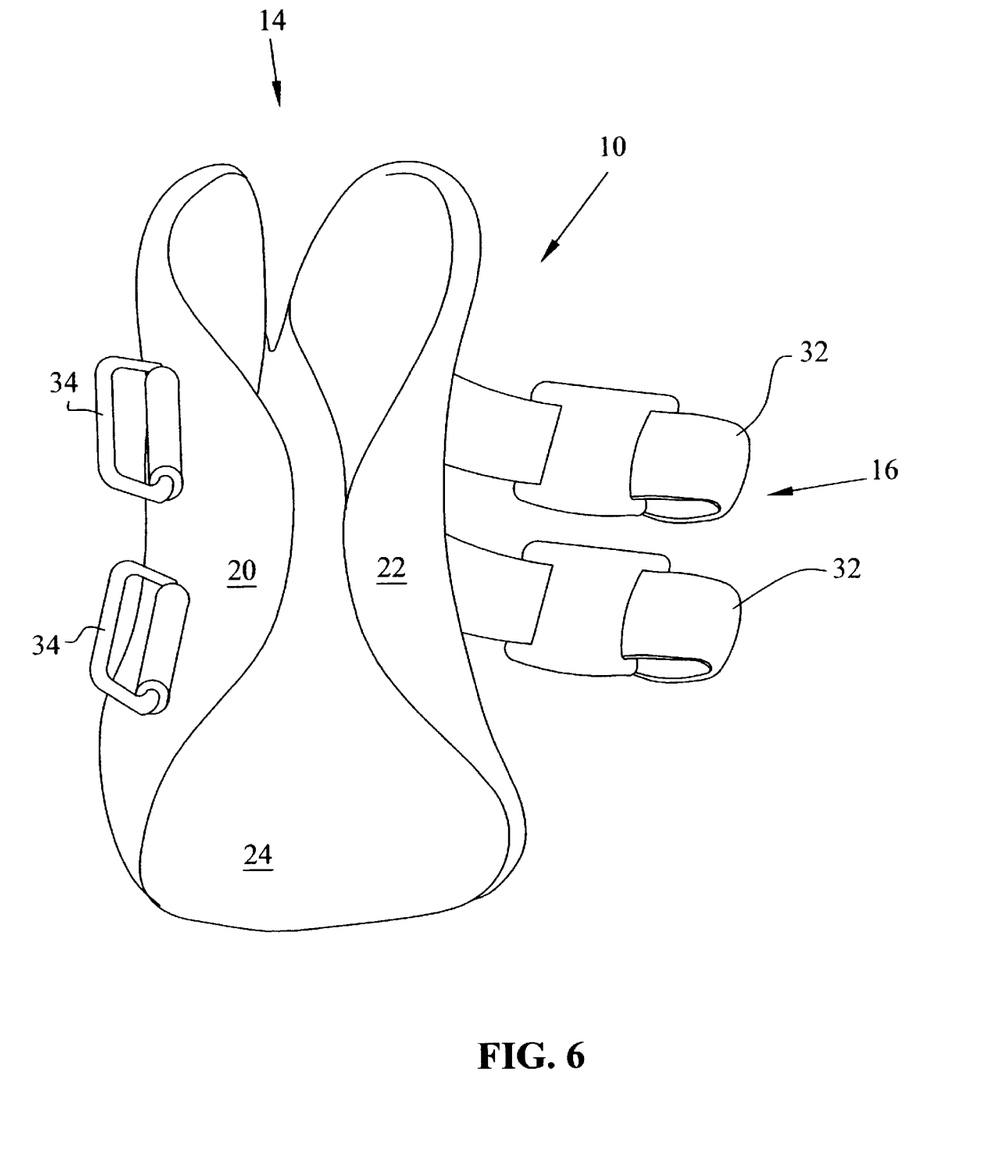
FIG. 6 is a front view of the foot orthotic.

Now referring to FIG. 5, it can be seen that the bottom 24 of pliable body 14 extends from a back heel 41 of the orthotic proximal to, but does not encompass, the first metatarsal head (ball of the foot) 40 of foot 12 on the medial side 22 of foot orthotic 10. On the lateral side 20 of foot orthotic 10, bottom 24 extends from the back of the heel 41 just distal to and encompassing the fifth metatarsal head 42 of foot 12.

In the preferred embodiment, securing mechanism 16 includes hook and loop straps 32 and looping rings 34. Hook and loop straps 32 are attached to the medial side 22 of pliable body 14 with rivets 36. On the opposing side of foot orthotic 10, looping rings 34 are attached to lateral sidewall 20 of pliable body 14 using ring clasps 39, which are riveted to lateral sidewall 20 with rivets 38.

Figure 1:
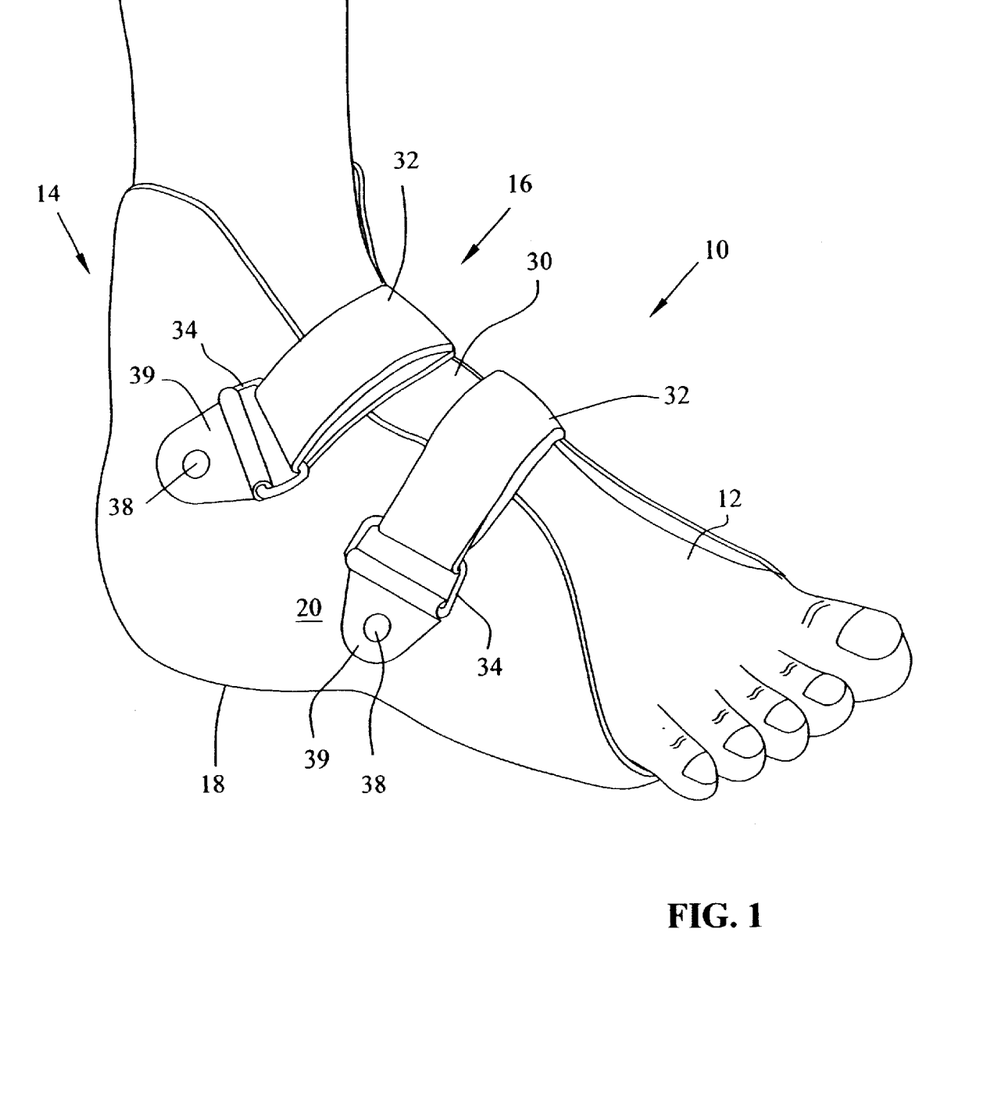
FIG. 1 is a perspective view of a foot in the foot orthotic shown from the lateral or exterior side of the foot.
Figure 2:
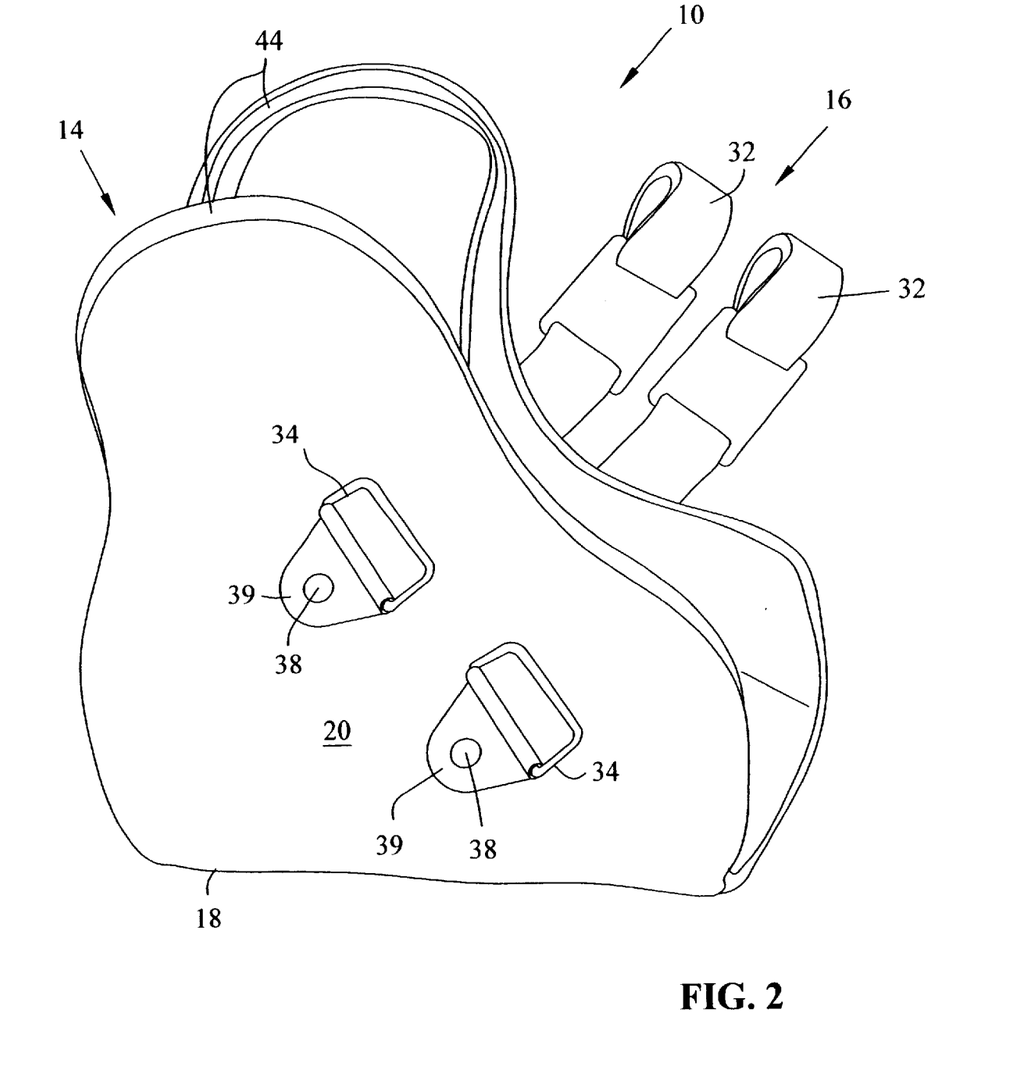
FIG. 2 is a perspective view of the foot orthotic from the lateral or exterior side.
Figure 3:
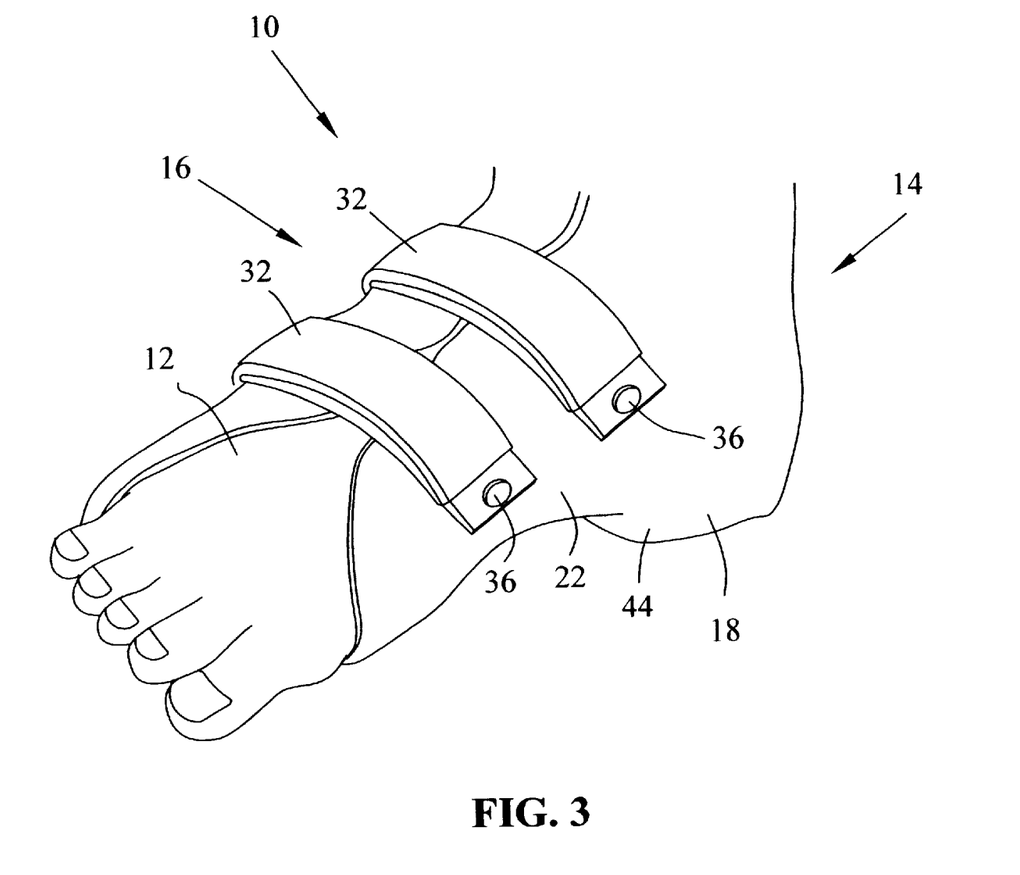
FIG. 3 is a perspective view of the foot in the foot orthotic from the medial or inner side of the foot.
Figure 4:
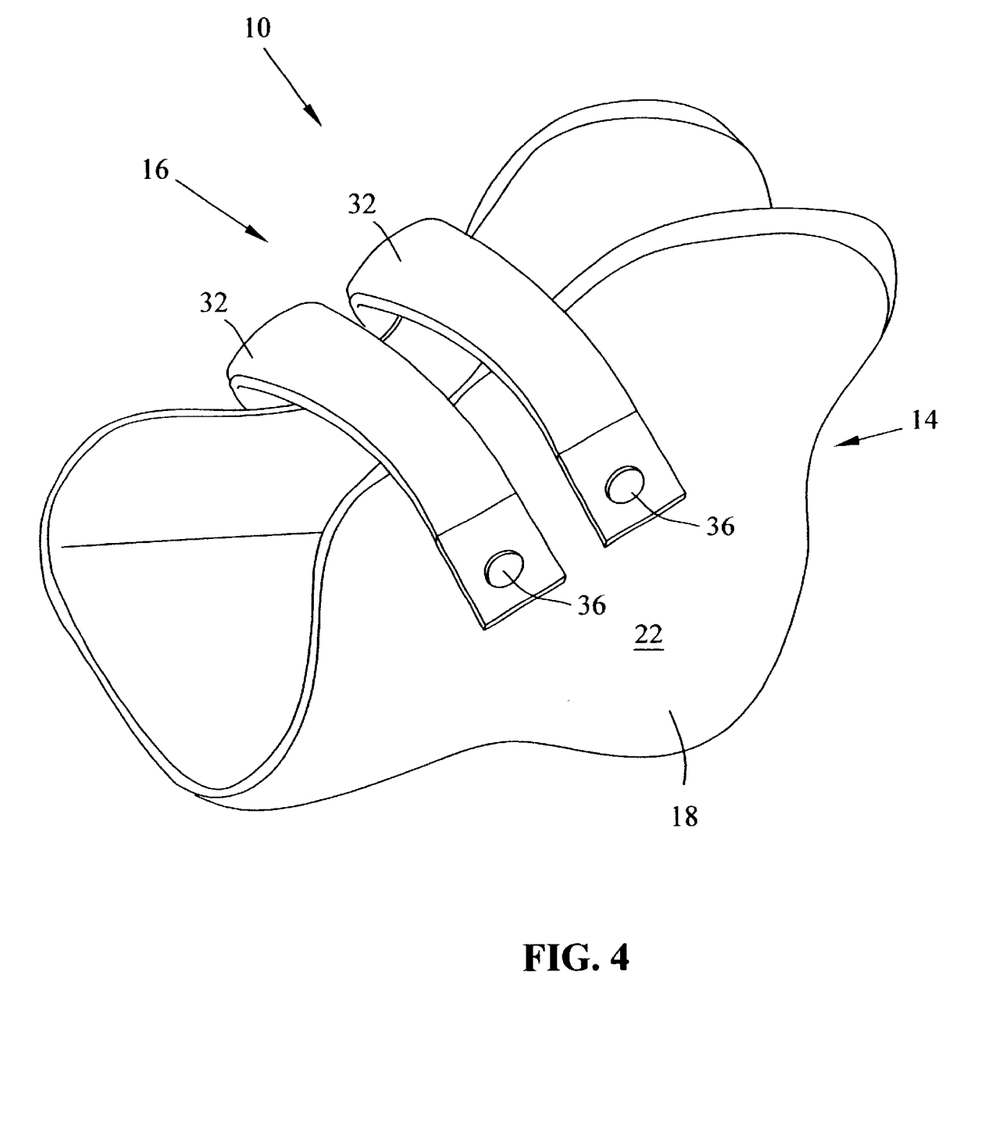
FIG. 4 is a perspective view of the foot orthotic from the medial side.

In order to provide increased stability for walking and standing, heel post 18 is attached to bottom 24. Heel post 18 is substantially flush with bottom 24 with the exception of a small ridge 44 on the medial side 22 of foot orthotic 10 that corresponds to the arch of the foot as shown in FIGS. 3 and 5.

Foam padding 44 is attached to the inside of pliable body 14 around the ankle area to provide additional comfort for the wearer. In addition, a foam pad or other support (not shown) may be attached to the inner portion 24a of the bottom of the pliable body 14 and the interior of medial sidewall 22 to provide additional arch support.

Having described the configuration, the fabrication of foot orthotic 10 will now be described. Generally, the fabrication of foot orthotic 10 starts by casting a mold about foot 12 using standard plaster cast techniques. After the cast hardens a single vertical cut spanning from the top to the bottom of the cast is made and the cast is pried open and removed from the foot. This single cut is resealed using standard plaster bandages. At this point, the cast represents a negative mold of foot 12.

The next step is to make a positive mold from the negative mold by filling the negative mold with a molding plaster. A pipe, rod or stick may be placed into the negative mold extending up to approximately 12 inches out of the top of the mold to provide a means to secure the mold during the modification and fabrication process. When the positive mold is totally cured, the negative mold is removed and discarded. The positive mold is then modified by adding smooth plaster build-ups of approximately ⅛" thick over the ankles, the posterior aspect of the heel, and any other areas corresponding to where bones protrude significantly. Adding the buildups provides additional room in the foot orthotic so as to prevent putting undue pressure on the bony prominences of the foot and ankle. The dorsum or top are of the foot and the instep are also built up approximately ⅛" to keep the edges of the foot orthotic from pinching the foot when worn. The positive model is then sanded smooth.

Several layers of nylon are then placed over the mold to facilitate the passage of air during the vacuum forming process. A sheet of vacuum formable thermoplastic large enough to cover the entire mold is then cut and placed in an oven to be heated to a formable temperature. There are several types and thicknesses of plastic that may be used for this fabrication including prosthetic grade polypropylene, polyethylene, and copolymer; however, the final product must be thin and pliable enough to wrap around the foot to provide hydrostatic pressure when tightened. As used in the preferred embodiment, prosthetic grade copolymer in a ¹⁄₁₆" thickness tends to produce an orthotic having the desired characteristics. One limitation to the preferred material and thickness of the invention though is that it is generally limited to and used with children weighing under 85 pounds as the flexibility inherent in pliable body 14 is not capable of providing adequate support for children or adults of greater weight.

In addition to the sheet of formable thermoplastic, a semi-circular piece of identical type material in approximately ¼" thickness is also placed in the oven. The semi-circular piece is cut out roughly to correspond to the size of the plantar or bottom surface of the heel and will be used as a heel post. When the plastic has reached the correct molding temperature of approximately 360 degrees Fahrenheit, the ¼" heel post is placed onto the sheet of plastic in a position so as to correctly align with the heel on the mold. The entire sheet is removed from the oven and drape molded and sealed over the positive mold. During the drape molding process, it is necessary to stretch the plastic as thin as possible without tearing so as to achieve a thin and pliable body 14. Air space between the plastic and the model is evacuated by way of a vacuum system and facilitated by the nylon layers between the positive mold and formable plastic.

After reaching room temperature, the formable plastic can be removed from the positive mold. The plastic is cut off using a cast cutter or sharp utility knife. The heel post 18 is sanded or ground into the shape of a heel and the plantar surface is ground flush with the plantar surface of the device with the exception that the small ridge 44 is usually left on the medial side 22 of the orthotic around the arch area. Grinding the heel post flush with bottom surface 24 of foot orthotic 10 adds stability in standing and walking for a wearer. The plastic mold is then trimmed in accordance with the dimensions of foot orthotic 10 as specified above.

The unique trim lines of foot orthotic 10 allow for normal toe off, stair climbing, squatting, walking and running, all of which are significantly impaired with 20 traditional bracing. All of the edges of the device are buffed to a smooth finish. Then, the hook and loop type fastening straps 32 and corresponding looping rings 34 are attached with rivets 36, 38.

In addition to the manufacturing sequence discussed above, it has also been found that foot orthotic 10 may be fabricated without the necessity of taking a cast mold of each user's foot. Instead, if a suitable number and variety of positive molds are maintained in inventory having varying lengths and widths, a proper foot orthotic 10 can be obtained by taking measurements of the pronated foot to receive an orthotic and matching the measurements to the closest mold. This is possible due to the fact that foot orthotic 10 uses a thin pliable body 14, allowing for some conformance to the foot, as opposed to the currently known rigid braces which must match exactly and require taking a cast of every pronated foot. Selected measurements of the pronated foot as described below are taken to the nearest ¹⁄₁₆" of the pronated foot. All measurements are taken snug but not tight with the child in a seated position facing the person taking the measurements.

Figure 8:
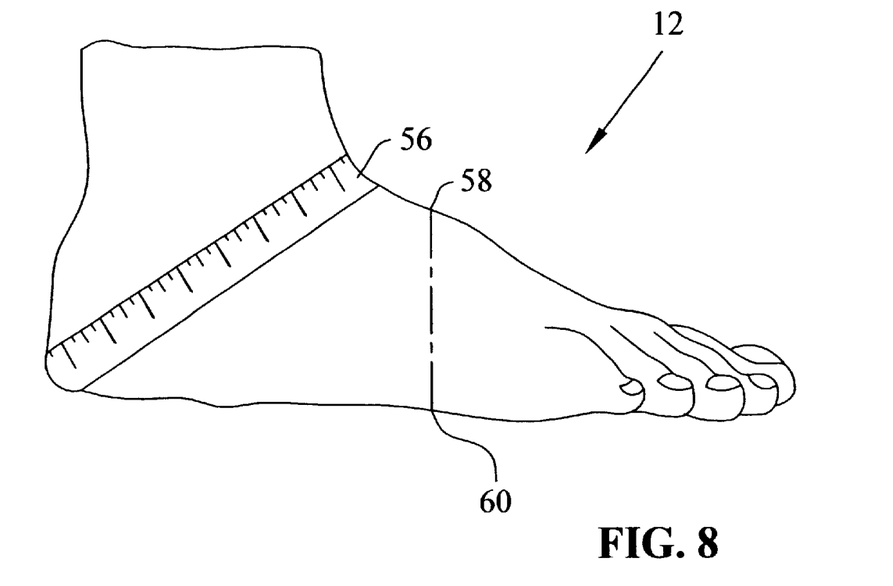
FIG. 8 is a side view of the foot.
Figure 9:
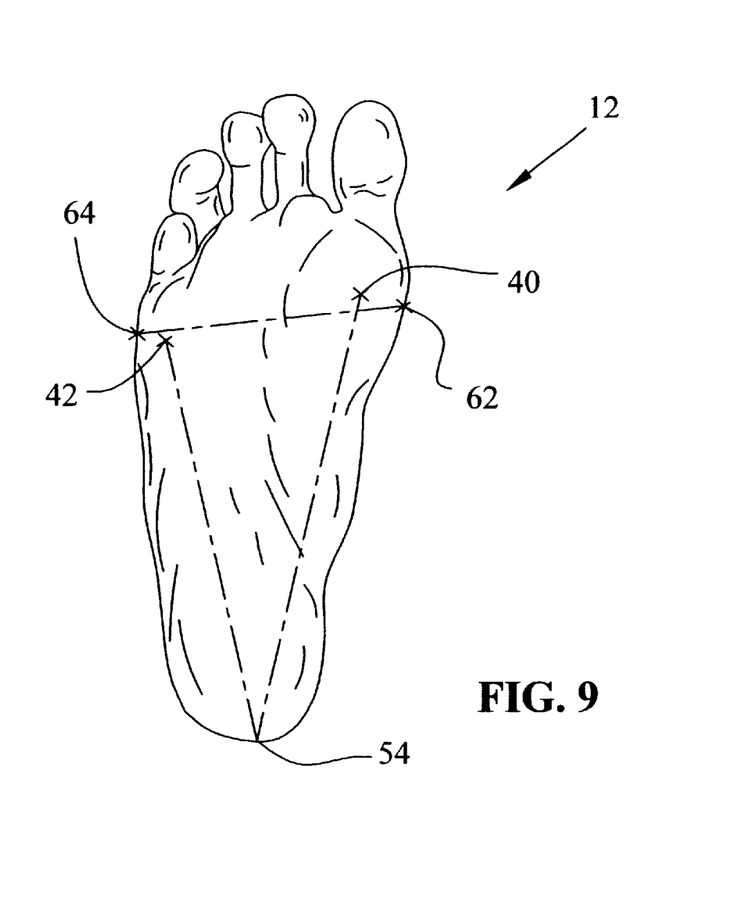
FIG. 9 is a bottom view of the foot.
Figure 10:
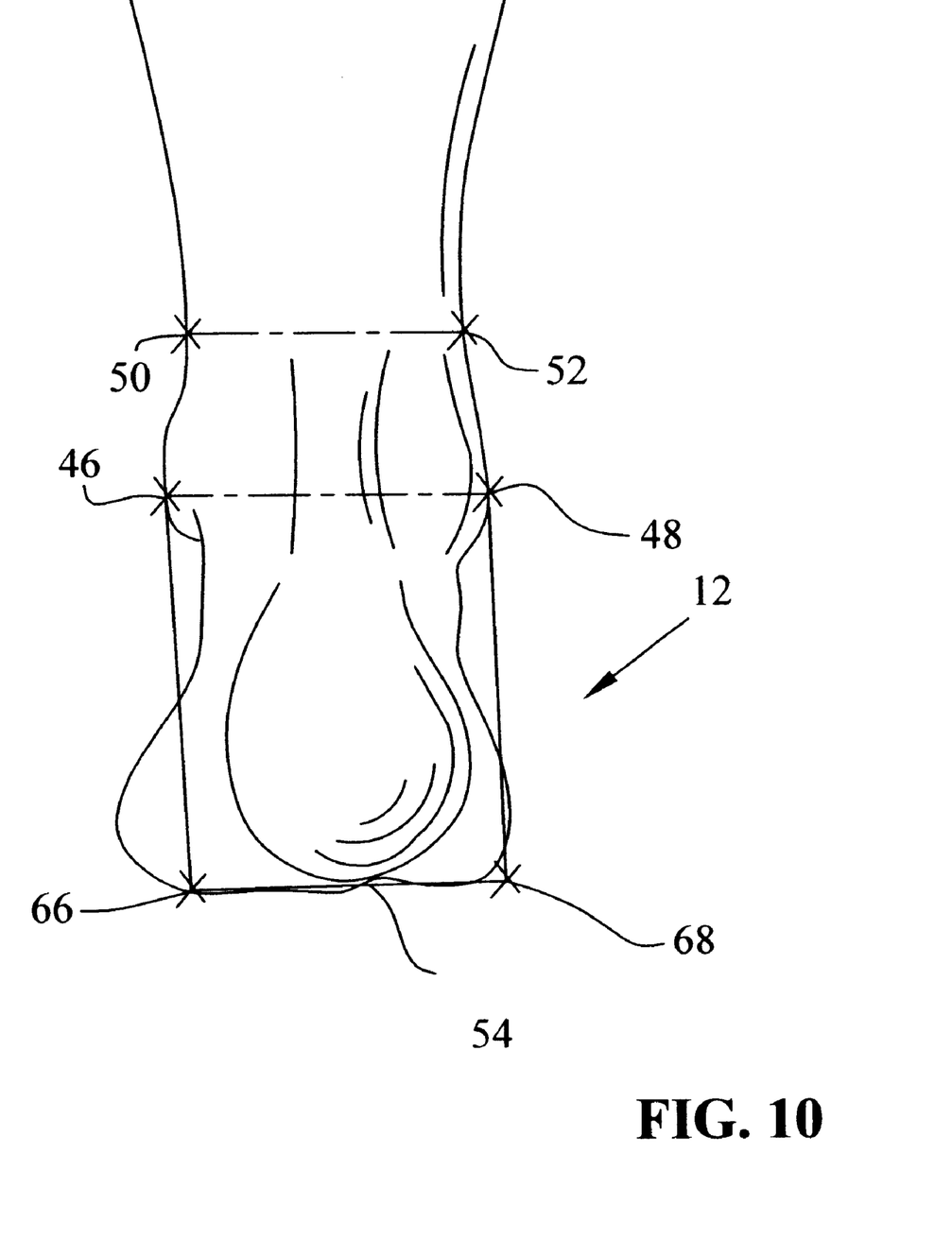
FIG. 10 is a rear view of the heel of the foot and ankle.

Now referring to FIGS. 8–10, a total of nine measurements are required. To start, the apex of the first metatarsal head 40 and the fifth metatarsal head 42 is marked on the pronated foot 12 with a washable marker or pen as well as the apex of the medial 46 and lateral 48 malleolus (ankle bone) on both feet before taking any measurements. The first measurement to be taken is a circumferential measurement of the smallest part of the leg just above the ankle along line 50, 52 as shown in FIG. 10. The circumferential measurements may be taken with a flexible tape measure 56. Next, a circumferential measurement is taken diagonally across the heel 54 of the foot and over the foot 12 using tape measure 56 as shown in FIG. 8. The final circumferential measurement is taken around the foot at the highest part of the medial longitudinal arch as indicated along line 58, 60.

Next, width measurements are taken using a caliper. The first width measurement is a measurement across the medial apex 46 and the lateral apex 48 of the ankle. Next, the width of the foot at the first and fifth metatarsal heads is taken along line 62, 64 while applying gentle pressure to press down on the foot thereby causing a slight splay as occurs during normal weight bearing.

Next, length measurements are taken including a measurement from the back of the heel 54 to the apex of the first metatarsal head 40 and from the back of the foot heel 54 to the apex of the fifth metatarsal head 42 as shown in FIG. 9. The remaining required measurements to fit a foot orthotic 10 are height measurements from beneath the heel 54 to the apex of the medial malleolus 46 (line 46, 66) and from the bottom of the heel 54 to the apex of the lateral malleolus 48 (line 48, 68).

From the measurements described above, a positive mold can be selected and a foot orthotic fabricated greatly diminishing the time and cost associated with casting a mold for every foot to be treated.

Although correct fabrication is crucial to correct operation of the device, accurate donning of the orthosis is equally important to its proper performance. Foot orthotic 10 is designed to be issued by prescription only, and must be fit originally by a trained health care professional. When donning, the orthotic 10 must be placed on the proper foot 12. Hook and loop straps 32 are then fed through loop and rings 34, and are drawn to a significant tightness so as to create a fluidic or hydrostatic pressure within the walls of the orthosis. Hook and loop straps 32 are demarcated with the marker indicating the proper placement of the hook and loop strap 32 within looping ring 34. This allows foot orthotic 10 to be donned at a later date and achieve the same pressure as at original fitting. Care must be taken at the initial fitting so that the orthotic 10 is not tightened excessively causing restriction of normal circulation in foot 12.

Having discussed the design, fabrication and fitting of the claimed invention, it will be obvious to one skilled in the art that numerous variations are possible without departing from the scope and spirit of the invention. For instance, the orthotic shown in FIGS. 1–7 is designed for a right foot. It should be noted that generally the orthotic will be worn in pairs on both the right and left foot of the wearer wherein the left orthotic would be a reverse configuration of the right orthotic. Furthermore, although the hook and loop straps 32 are shown attached to the medial side 22 and the looping rings 34 attached to the lateral side 20, it should be obvious that the looping rings 34 may be attached to the medial side 22 and the hook and loop straps 32 to the lateral side 20. Furthermore, in some small patients, it has been found advantageous to have one looping strap 32 attached to the medial side 22 and one looping strap 32 attached to the lateral side 20. In addition, hook and loop straps 32 may be attached to pliable body 14 using other than rivets 32 such as glue or stitching, or the securing straps may even be formed integrally into pliable body 14. Also, other securing mechanisms well known in the art, such as buckles or snaps may be substituted for the hook and loop type fasteners. Casting mold materials may also vary. In the preferred embodiment plaster casts and molds are used but any other suitable mold material such as polyurethane may be substituted.

Although the invention has been taught with specific reference to the preferred embodiment, someone skilled in the art will recognize that changes can be made in form and detail without departing from the spirit and scope of the invention. The described embodiments are to be considered only as illustrative and not restrictive. The scope of the invention is, therefore, indicated by the appended claims rather than by the foregoing description.

What is claimed is:

1. A foot orthotic for correction of foot pronation, comprising a thin formable plastic body having pliable medial and lateral side walls and a pliable bottom, and a securing mechanism to draw said side walls about a foot so as to create a hydrostatic pressure of the soft tissue of the foot within the orthotic, the pliable body being shaped to rise above the ankles of a user and to dip down to a posterior point at the top of the user's heel creating a narrow posterior gap.

2. The foot orthotic as set forth in claim 1, wherein the securing mechanism includes hook and loop straps attached to the pliable body.

3. The foot orthotic as set forth in claim 2, wherein the securing mechanism further includes looping rings attached to the pliable body for wrapping the straps therethrough.

4. The foot orthotic as set forth in claim 1, wherein the formable plastic is chosen from the group consisting essentially of polypropylene, polyethylene or copolymer.

5. The foot orthotic as set forth in claim 1, further comprising a heel post attached to the bottom of the foot orthotic to provide stability for standing or walking.

6. The foot orthotic as set forth in claim 5, wherein the heel post is formed from a semi circular piece of material chosen from the group consisting essentially of polypropylene, polyethylene, or copolymer.

7. A foot orthotic for correction of foot pronation, comprising a thin formable plastic body having pliable medial and lateral side walls and a pliable bottom, and a securing mechanism to draw said side walls about a foot so as to create a hydrostatic pressure of the soft tissue of the foot within the orthotic, said pliable body being sized to wrap partly over the dorsum of the foot on both the medial and lateral side thereof to define a narrow gap between the medial and lateral walls thereof, said narrow gap coinciding with the dorsum of a user's foot as said pliable body is wrapped about the foot.

8. A method of making a foot orthotic comprising the steps of providing a positive mold of a foot chosen from among a number of preexisting molds and sized from selective measurements taken from a pronated foot, providing a formable thermoplastic, heating said thermoplastic, molding and stretching said thermoplastic about said positive mold to make a thin, pliable body capable of being wrapped around a foot so as to create hydrostatic pressure therein, the selective measures including width measurements across the ball of the foot taken in semi-weight bearing mode and across the apex of the ankle of the foot, and length measurements from the first metatarsal head of the foot to the back of the heel, and from the fifth metatarsal head to the back of the heel.

9. The method of making a foot orthotic as set forth in claim 8, wherein the thin, pliable body is stretched to less than 1/16 inch in thickness and further comprising the step of providing a securing mechanism attached to said pliable body for drawing the pliable body tightly about the foot.

10. The method of making a foot orthotic as set forth in claim 8, wherein the the positive mold is created by the steps comprising forming a cast about the foot, removing the cast from the foot to form a negative mold of the foot, providing molding material, and filling said negative mold with said molding material from the positive mold.

11. The method of making a foot orthotic as set forth in claim 8, further comprising the step of building up the mold in areas that correspond to ankles, a posterior aspect of the heel, and other areas of the positive mold corresponding to where the foot has bones that protrude significantly.

12. The method of making a foot orthotic as set forth in claim 8, further comprising the step of building up a dorsum area and instep area of the positive mold.

13. The method of making a foot orthotic as set forth in claim 8, further comprising the step of heating a heel post of formable thermoplastic and placing said heel post on a position of the orthotic corresponding to the heel of the foot.

14. The method of making a foot orthotic as set forth in claim 13, further comprising the step of surface finishing the heel post into the shape of a heel such that the bottom surface of the heel post is flush with a bottom surface of the pliable body.

15. A method of making a foot orthotic comprising the steps of providing a positive mold of a foot chosen from among a number of preexisting molds and sized from selective measurements taken from a pronated foot, providing a formable thermoplastic, heating said thermoplastic, molding and stretching said thermoplastic about said positive mold to make a thin pliable body capable of being wrapped around a foot so as to create hydrostatic pressure therein, said thermoplastic being molded about said positive mold by draping said heated thermoplastic about said positive mold and stretching said thermoplastic as thin as possible without tearing so as to achieve a thin and flexible pliable body.

16. The method of making a foot orthotic as set forth in claim 15, further comprising the step of evacuating air space between the thermoplastic and the positive mold using a vacuum system.

17. The method of making a foot orthotic as set forth in claim 8, further comprising the step of trimming the thermoplastic formable body corresponding to above a wearer's ankle and down posteriorly to the top of the heel of the wearer leaving a narrow opening on the posterior aspect between the top of the heel and the top of the orthosis.

18. The method of making a foot orthotic as set forth in claims 8, further comprising the step of trimming said formable body so that said formable body will wrap partially over the dorsum of the foot on both the medial and lateral sides thereof.

19. The method of making a foot orthotic as set forth in claim 8, further comprising the step of trimming said formable body so as to provide a narrow gap between the medial and lateral walls of the formable body when said formable body is wrapped about the foot.

20. The method of making a foot orthotic as set forth in claim 8, further comprising the step of trimming said formable body medially to extend just proximal to but not encompassing the first metatarsal head of the foot and laterally just distal to and encompassing the fifth metatarsal head of the foot.

* * * * *